United States Patent [19]

Kholodov et al.

[11] 4,245,100
[45] Jan. 13, 1981

[54] SYDNONIMINE N-ACYL DERIVATIVES AND METHOD FOR PREPARING SAME

[75] Inventors: Leonid E. Kholodov; Vladimir G. Yashunsky; Roald A. Altshuler; Mikhail D. Mashkovsky; Valentina V. Ogorodnikova; Zoya A. Olovyanishnikova, all of Moscow; Anna S. Vitvitskaya, Leningrad; Valery A. Parshin; Ekaterina A. Kelekhsaeva, both of Moscow, all of U.S.S.R.

[73] Assignees: Vsesojuzny nauchno-issledovatelsky khimikofarmatsevtichesky institut imeni S. Ordzhonikidze; Institut biofiziki, both of Moscow, U.S.S.R.

[21] Appl. No.: 855,246

[22] Filed: Nov. 28, 1977

[51] Int. Cl.³ .................. A61K 31/42; C07D 271/04
[52] U.S. Cl. .................................. 548/125; 424/272
[58] Field of Search .................. 260/307 F; 548/125

[56] References Cited

U.S. PATENT DOCUMENTS

| | | | |
|---|---|---|---|
| 3,277,108 | 10/1966 | Daeniker | 260/307 |
| 3,833,580 | 9/1974 | Gotz | 260/247.2 A |

FOREIGN PATENT DOCUMENTS

| | | |
|---|---|---|
| 961628 | 6/1964 | United Kingdom . |
| 962293 | 7/1964 | United Kingdom . |
| 963459 | 7/1964 | United Kingdom . |
| 1262830 | 2/1972 | United Kingdom . |

*Primary Examiner*—Donald G. Daus
*Assistant Examiner*—Lisa Jones
*Attorney, Agent, or Firm*—Lackenbach, Lilling & Siegel

[57] ABSTRACT

N-acyl sydnonimines of the formula:

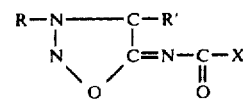

wherein R is phenyl, β-phenylethyl, dl-α-methyl-β-phenylethyl or l-α-methyl-β-phenylethyl; R' is hydrogen, phenyl; X is a lower alkyl, phenyl,

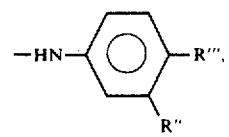

wherein R" is hydrogen, a halogen, a lower fluorinated alkyl; R''' is hydrogen, a halogen, a lower alkyl; when R is dl-α-methyl-β-phenylethyl, R' is H, R" is Cl, R''' is only Cl, while when R' is H, X is NHC₆H₅ R is only l-α-methyl-β-phenylethyl; when X is phenyl, R and R' are each phenyl only.

The method for preparing sydnonimine N-acylderivatives comprises reacting N-nitrosoderivatives of N-substituted nitriles of α-aminoacids of the formula:

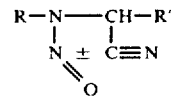

wherein R is phenyl, β-phenylethyl, di-α-methyl-β-phenylethyl or l-α-methyl-β-phenylethyl; R' is H, phenyl; when R' is phenyl R is phenyl only, with an acylation agent in a solvent medium in the presence of a basic-character catalyst, followed by isolation of the desired product.

11 Claims, No Drawings

SYDNONIMINE N-ACYL DERIVATIVES AND METHOD FOR PREPARING SAME

FIELD OF APPLICATION

The present invention relates to novel compounds, viz. sydnonimine derivatives and a method for preparing same. These compounds possess pronounced psychostimulant activity when administered to mammals.

BRIEF SUMMARY OF THE INVENTION

The sydnonimine N-acyl derivatives according to the present invention are novel compounds hitherto unknown in the literature.

In accordance with the present invention, novel sydnonimine N-acyl derivatives have the formula:

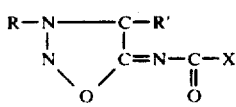

wherein R is phenyl, $\beta$-phenylethyl, dl-$\alpha$-methyl-$\beta$-phenylethyl or l-$\alpha$-methyl-$\beta$-phenylethyl; R' is hydrogen, phenyl; X is a lower alkyl, phenyl,

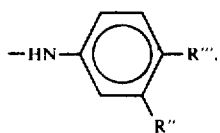

wherein R'' is hydrogen, a halogen, a lower fluorinated alkyl; R''' is hydrogen, a halogen, a lower alkyl; when R is dl-$\alpha$-methyl-$\beta$-phenylethyl, R' is H, R'' is Cl, R''' is only Cl; when R' is H, X = $NHC_6H_5$, R is only l-$\alpha$-methyl-$\beta$-phenylethyl; when X is phenyl, R and R' are each only phenyl.

These compounds are white or white with a yellowish tint crystalline substances stable in the air, sparingly soluble in water, soluble in chloroform and less soluble in alcohol.

DETAILED DESCRIPTION OF THE INVENTION

Psychostimulating activity of the compounds according to the present invention has been tested in experiments with mice and rats.

The experiments are performed with white male mice with a weight of 18-20 g and with white rat males with a weight of 120 to 140 g with the account of parameters characterising the influence of the compounds according to the present invention on the central nervous system as well as toxicity. Following this objective, there have been studied:

(1) effect of the compounds on the locomotory activity of the animals (locomotory activity is registered using the instrument "Animex");

(2) capability of the compounds of inducing sterotypic behavior reactions;

(3) capability of enhancing a reflex excitability of the animals with respect to the use of tactile stimuli (air jet pointed from a syringe to an animal);

(4) acute (24-hours) toxicity of the compounds in individually kept mice and mice placed into standard cages with 10 animals in each cage, i.e. so-called "group toxicity".

To quantitatively evaluate the central stimulant activity of the compounds in the tests on mice the values of $ED_{200}$ (locomotion) are determined, i.e. doses in which the compounds cause a two-fold potentiation of locomotory activity of the animals; in the tests performed with rats there are determined values of $ED_{50}$ (stereotypy), i.e. doses in which the compounds, one hour after their administration, cause, in 50% of the test rats, stereotypic behavior reactions ($ED_{50}$ doses are calculated by the Litchfield and Wilkoxsons method).

The compounds according to the present invention are sparingly soluble in water. They were administered to the animals in the form of a suspension prepared with the use of a 1% solution of carboxymethylcellulose with the addition of Tween-80 ® as an emulsifying agent. Since molecular weights of the test compounds differ from each other, their doses are calculated in mcM/kg.

The compounds according to the present invention provide an exciting effect in the central nervous system which is demonstrated in mice and rats by an enhanced locomotory activity. Thus, minimal doses, which permanently cause a pronounced locomotory hyperactivity in the animals, of the above-mentioned compounds of the formula (1), wherein R is $PhCH_2CH_2$ or R is dl-$PhCH_2(CH_3)CH$; with R'=H and X=$NHC_6H_4Cl$-para, or X=$NHC_6H_3Cl_2$-meta, para-are 7 to 10 mcM/kg, while for the compounds of the formula (1) with R=dl-$PhCH_2(CH_3)CH$, R'=H, at X=NH-$C_6H_4CH_3$-meta or X=NH-$C_6H_4CH_3$-para and for the compounds of the formula (1) with R=$C_6H_5CH_2CH_2$, R'=H, X=NH-$C_6H_4CF_3$-meta, minimal active doses are 15 to 20 mcM/kg. The stimulant effect of these doses is observed after 10-15 minutes after administration reaching its maximum after 30-35 minutes at a total duration of the effect of 1.5-2 hours. When these doses are increased by 3-4 times (with mice) and 1.5-2 times (with rats), the intensity and duration of the locomotory hyperactivity is also increased. Further increase in doses results in the origination of stereotypic behavior reactions with the animals which is manifested by swing motions of the head and fore limbs, smelling and licking the cage floor. The stereotypy duration at high doses is 6 to 8 hours.

In a special series of experiments there has been made a quantitative comparison of the central stimulant effect of the compounds according to the present invention as determined by tests of locomotory activity with mice and stereotypy with rats. Certain results of these experiments are presented in the following Table.

TABLE

Activity of the compounds of the formula (1): R=dl-$C_6H_5CH_2(CH_3)CH$, R'=H, as by tests for locomotory excitation with mice ($ED_{200}$) and and stereotypic behavior with rats ($ED_{50}$).

| Compounds of the present invention | $ED_{200}$ (locomotion) for mice, mcM/kg | $ED_{50}$ (stereotypy), for rats, mcM/kg |
|---|---|---|
| of the formula (1) wherein: | | |
| X = NH—$C_6H_4Cl$—para | 18.2 | 20.0 |
| X is NH—$C_6H_4$—$CH_3$—meta | 32.3 | 39.9 |

The compound of the formula (1) according to the present invention, wherein R is 1-PhCH$_2$(CH$_3$)CH, R'=H, X=NHC$_6$H$_5$ in doses of from 3 to 5 mcM/kg causes a moderate tactile hyperreflexia and in doses of from 6 to 8 mcM/kg, an acute tactile hyperreflexia. The latter is clearly pronounced with mice by a series of strong sudden jumps occurring right at the moment of contact with the air jet. Within the doses range of from 9 to 80 mcM/kg this compound increases the locomotory activity of mice in the direct relationship between this effect value and dose logarithm. The locomotory activity value is doubled upon administration of the dose of ED$_{200}$ within the range of from 30 to 35 mcM/kg. With the dose of 40 mcM/kg, the increase in the locomotory activity reaches its maximum within 20 to 30 minutes after the compound administration and is maintained at this level during the next 1-1.5 hour.

In tests on mice, minimal lethal doses (i.e. doses killing 10 to 20% of the test animals) of the compounds according to the present invention are within the range of from 200 to 2,000 mcM/kg which is by 25–100 times higher than the dosage causing a clearly pronounced pharmacological activity-locomotory hyper-activity of mice. It should be noted that toxicity of the compounds is not increased upon administration of the test compounds to the group-housing animals, i.e. there is no phenomenon of "group toxicity" which is characteristic for a series of known psychostimulant compounds such as amphetamine or dextramphetamine.

Therefore, the compounds according to the present invention are low in toxicity and in small doses cause an intensive excitation of animals which is characteristic of psychostimulant preparations.

Known in the art is a derivative of sydnonimine, i.e. dl-N-phenylcarbamoyl-3-(α-methyl-β-phenylethyl) sydnonimine which also possesses a psychostimulant activity. Comparison of this prior art compound with those of the present invention shows however, that the novel compounds according to the present inventions are 2-4 times as active as those of the prior art in experiments with animals. Thus, the known compound, i.e. dl-N-phenylcarbamoyl-3-(α-methyl-β-phenylethyl) sydnonimine is characterized by values of ED$_{200}$ of 72.6 mcM/kg (for locomotion) and ED$_{50}$ of 107.1 mcM/kg (for stereotype); this means that to achieve the same pharmacological effect, it is necessary to administer doses 2-4 times as high as those of the compounds according to the present invention.

Most active among the compounds according to the present invention include, for example:

1-3-(α-methyl-β-phenylethyl)-N-phenylcarbamoyl-sydnonimine of the formula:

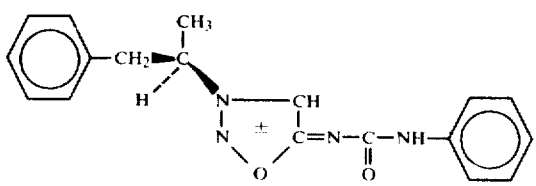

l-N-para-chloro-phenylcarbamoyl-3-(α-methyl-β-phenylethyl) sydnonimine of the formula:

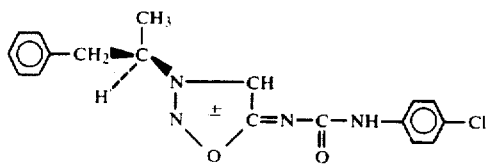

N-para-chlorophenylcarbamoyl-3-(β-phenylethyl) sydnonimine of the formula:

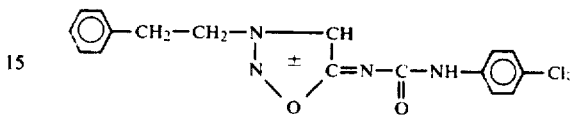

dl-N-para-chlorophenylcarbamoyl-3-(α-methyl-β-phenylethyl)sydnonimine of the formula:

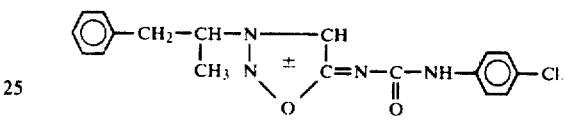

The novel N-acyl derivatives of sydnonimine according to the present invention are prepared by reacting N-nitro derivatives of N-substituted nitriles of α-aminoacids of the formula:

wherein R is phenyl, β-phenylethyl, dl-α-methyl-β-phenylethyl, l-α-methyl-β-phenylethyl; R' is H, phenyl; when R' is phenyl, R is phenyl only;

with an acylation agent in a solvent medium in the presence of a basic-character catalyst, followed by isolation of the desired product. As the acylation agent it is advisable to use haloanhydrides, anhydrides of carboxylic acids or arylisocyanates. It is preferable to use, as the solvent, benzene, toluene, dichloroethane. As the catalyst use can be made of various bases; however, it is better to use, as the catalyst, triethylamine, dimethylbenzylamine, N-methylmorpholine. The reaction is conducted both at room temperature and upon heating, depending on the acylation agent activity. It is preferable to conduct the reaction at a temperature within the range of about 40° to 60° C.

The method according to the present invention is performed in the following manner:

To a solution of N-nitrosoderivatives of N-substituted nitriles of α-aminoacids of the formula (II) there are added a basic-character catalyst and an acylation agent. The reaction mixture is preferably heated to a temperature within the range of from 40° to 60° C. to accelerate the process.

On completion of the reaction the desired product is recovered from the reaction mass by conventional methods.

As the acylation agents in the reaction according to the present invention various electrophilic reagents can be used such as anhydrides and chloroanhydrides of carboxylic acids, arylisocyanates. As the catalyst use can be made of various bases; it has been found that most suitable for the acceleration of the reaction is triethylamine. The reduction proceeds slightly slower in the presence of dimethylbenzylamine, N-methylmorpholine. Other bases can also be used, such as imidazole, pyridine, quinoxaline and the like. The reaction speed substantially depends on the solvent employed while being increased (in the case of triethylamine as the catalyst) in the series: chloroform > hexane > toluene > benzene > chlorobenzene > 0-dichlorobenzene > 1,2-dichloroethane > nitrobenzene. It is preferred to use toluene or benzene, since the starting compounds are very soluble in these solvents, whereas the reaction products, i.e. corresponding N-acyl derivatives of sydnonimine, are not soluble, as a rule, in these particular solvents, wherefore they are precipitated in their pure form. The reaction can occur in water, but in this case the acylation agent vigorously reacts with water; for this reason, it is more suitable to conduct the reaction in organic hydroxyl-free solvents.

The reaction can be performed at room temperature, especially in the case of active acylation agents; however, the process rate is rapidly increased with increasing temperature. At high temperatures there may occur a thermal decomposition of the starting nitroso derivative, therefore it is preferable to carry out the process at a temperature within an optimal range of about 40° to 60° C. The desired product yield ranges from 80 to 90% of the theoretical.

For a better understanding of the present invention, some specific Examples illustrating the method for preparing the novel N-acyl derivatives of sydnonimine are given hereinbelow.

EXAMPLE 1

To a solution of 5 g of dl-N-nitroso-N-($\alpha$-methyl-$\beta$-phenylethyl)-aminoacetonitrile in 70 ml of dry benzene there are added 6.7 ml of triethylamine and 5.95 ml of acetic anhydride. After heating for 3 hours at a temperature of 50° C. the reaction mass is evaporated to dryness; the residue is ground with ether; the precipitate is filtered-off, washed with water to give 5.3 g (83.5%) of dl-N-acetyl-3-($\alpha$-methyl-$\beta$-phenylethyl) sydnonimine melting at 98°-99° C. Found, %: C 63.46; H 6.18; N 17.04. $C_{13}H_{15}N_3O_2$. Calculated, %: C 63.60; H 6.16; N 17.12.

EXAMPLE 2

To a solution of 1 g of dl-N-nitroso-N-phenyl-$\alpha$-aminophenylacetonitrile in 10 ml of dry benzene there are added 1.15 ml of triethylamine and 0.49 ml of benzoyl chloride. The reaction mass is evaporated to dryness and the mixture is stirred for 3 hours at a temperature of 50° C.; the residue is treated with dry ether; the precipitate is filtered off and washed with water. The yield of N-benzoyl-3, 4-diphenylsydnonimine is 0.87 g; melting point is 185°-187° C. (with decomposition). Found, %: C 73.75 H 4.46 N 11.73. $C_{21}H_{15}N_3O_2$. Calculated, %: C 73.90; H 4.44; N 12.31.

EXAMPLE 3

To a solution of 0.70 g of l-N-nitroso-N-($\alpha$-methyl-$\beta$-phenylethyl) aminoacetonitrile in 7 ml of dry benzene there are added 0.65 ml of triethylamine and 0.42 ml of phenylisocyanate; the mixture is heated for 3 hours at a temperature of 50° C.; then it is cooled. The precipitate is filtered off, washed with benzene, dried and recrystallized from isopropanol to give 0.96 g (86.5%) of the desired product i.e. l-3-($\alpha$-methyl-$\beta$-phenylethyl)-N-phenylcarbamoylsydnonimine comprising a white powder with a yellowish tint substantially insoluble in water but soluble in fats, acetone, chloroform; its melting point is 150°-152° C. (with decomposition); specific rotation $[\alpha]_D^{20} = -254.5°$ (acetone, c = 1); it has three maximum points in UV-spectrum: $\lambda_{max} = 204$ nm, 259 nm, 341 nm (ethanol). Found, %: C, 67.41; H 5.74; N 17.23. $C_{18}H_{18}N_4O_2$. Calculated, %: C 67.06; H 5.63; N 17.38.

EXAMPLE 4

A solution of 2.03 g (0.01 mol) of dl-N-nitroso-N-($\alpha$-methyl-$\beta$-phenylethy)-aminoacetonitrile, 1.54 g (0.01 mol) of parachlorophenylisocyanate and 1.41 ml (0.01 mol) of triethylamine in 20 ml of dry benzene is heated for 4 hours at a temperature of 50° C.; then the solution is cooled. The precipitate is filtered off, washed with benzene to give 3.0 g (85.4%) of dl-N-para-chlorophenyl carbamoyl-3-($\alpha$-methyl-$\beta$-phenylethyl) sydnonimine, melting at 218°-130° C. (decomposition). Found, %: C 60.60; H 4.92; N 15.47. $C_{18}H_{17}ClN_4O_2$. Calculated, %: C 60.59; H 4.79: N; 15.70. IIR-spectrum, $cm^{-1}$: 1,645; 1.590; 1,530; 3,140. PMR-spectrum (in $CDCl_3$ relative to TMS), $\delta 8.10$ ppm; 9.30 ppm.

EXAMPLE 5

The process is conducted in a manner similar to that described in the foregoing Example 4, except that as the catalyst use is made of 5 ml of dimethylbenzylamine (instead of triethylamine); the yield of the desired product is 85% by weight of the theoretical value.

EXAMPLE 6

The process is conducted in a manner similar to that described in Example 4 hereinbefore, except that as the catalyst use is made of 6 ml of N-methylmorpholine (instead of triethylamine); the yield of the desired product is 85% of the theoretical value.

EXAMPLE 7 dl-N-nitroso-N-($\alpha$-methyl-$\beta$-phenylethyl) aminoacetonitrile is reacted with meta-, para-dichlorophenylisocyanate following the procedure described in Example 4 at a temperature of 40° C. There is obtained dl-N-metal, para-dichlorophenylcarbamoyl-3-($\alpha$-methyl-$\beta$-phenylethyl) sydnonimine; the yield is 88% of the theory; melting point is 128°-129° C. (with decomposition). Found, %: C 54.92; H 3.85; N 13.94. $C_{18}H_{16}Cl_2N_4O_2$. Calculated, %: C 55.20; H 4.13; N 14.31. IR-spectrum, $cm^{-1}$: 1,645; 1,580; 1,515. PMR-spectrum (in $CDCl_3$ relative to TMS) $\delta 8.12$, 9.52 ppm.

EXAMPLE 8 dl-N-nitroso-N-($\alpha$-methyl-$\beta$-phenylethyl)aminoacetonitrile is reacted with meta-trifluoromethylphenylisocyanate in a manner similar to that described in Example 4 hereinbefore. There is obtained dl-N-meta-trifluoromethylphenylcarbamoyl-3-($\alpha$-methyl-$\beta$-phenylethyl)sydnonimine; the yield is 81.5% of the theory; melting point is 150°-152° C. (with decomposition). Found, %: C 58.22; H 5.10; N 14.26. $C_{19}H_{17}F_3N_4O_2$. Calculated, %: C 58.50; H 4.10; N, 14.37. IR-spectrum, $cm^{-1}$: 1,642; 1,595; 1,540, 3,168. PMR-spectrum (in $CDCl_3$, relative to TMS) $\delta$: 8.14; 9.56 ppm.

EXAMPLE 9

N-nitroso-N-(β-phenylethyl aminoacetonitrile is reacted with meta-para-dichlorophenylisocyanate following the procedure described in Example 4 hereinbefore. There is obtained N-meta-, para-dichlorophenylcarbamoyl-3-(β-phenylethyl) sydnonimine; the yield is 85.5% of the theory; melting point is 137°-138° C. (with decomposition). Found, %: C 54.26; H 3.97; N 14.95. $C_{17}H_{14}Cl_2N_4O_2$. Calculated, %: C 54.12; H 3.74; N 14.85. IR-spectrum, $cm^{-1}$: 1,653; 1,580; 1,510. PMR-spectrum (in $CDCl_3$ relative to TMS), δ: 8.08; 9.52 ppm.

EXAMPLE 10

N-nitroso-N-(β-phenylethyl)aminoacetonitrile is reacted with meta-trifluoromethylphenylisocyanate following the procedure described in the foregoing Example 4 to give N-meta-trifluorophenyl carbamoyl-3-(β-phenylethyl)-sydnonimine; the yield is 82.2% of the theoretical value; melting point is 143°-145° C. (with decomposition). Found, %: C 57.60; H 4.12; N 14.59. $C_{18}H_{15}F_3N_4O_2$. Calculated, %: C 57.30; H 4.02; N 14.89. IR-spectrum, $cm^{-1}$: 1,640; 1,595; 1,538; 3,165. PMR-spectrum (in $CDCl_3$ relative to TMS), δ8.12; 9.52 ppm.

EXAMPLE 11 dl-N-nitroso-N-(α-methyl-β-phenylethyl-)aminoacetonitrile is reacted with para-tolylisocyanate following the procedure described in Example 4 at a temperature of 60° C. There is obtained dl-N-para-tolyl-carbamoyl-3-(α-methyl-β-phenylethyl)sydnonimine; the yield is 85% of the theoretical value; melting point is 128°-130° C. (with decomposition) Found, %: C 67.62; H 5.91; N 16.62. $C_{19}H_{20}N_4O_2$. Calculated, %: C 67.91; H 5.93; N 16.63. IR-spectrum, $cm^{-1}$: 1,645; 1,595; 1,540. PMR-spectrum (in $CDCl_3$ relative to TMS) δ8.10; 9.07 ppm.

EXAMPLE 12

The process is conducted in a manner similar to that described in Example 4, except that toluene is used as a solvent. The yield of the desired product is 86% of the theoretical value.

EXAMPLE 13

The process is conducted in a manner similar to that described in the foregoing Example 4, except that dry dichloroethane is used as a solvent. On completion of the reaction, the reaction mass is evaporated to dryness; the residue is ground in ether, filtered-off and recrystallized from isopropanol. The yield of the desired product is 80% of the theoretical value.

What is claimed is:

1. An N-acyl sydnonimine of the formula:

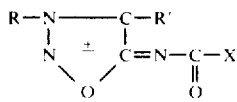

wherein R is selected from the group consisting of β-phenylethyl, dl-α-methyl-β-phenylethyl and l-α-methyl-β-phenylethyl; R' is selected from the group consisting of hydrogen and phenyl; X is selected from the group consisting of lower alkyl, and

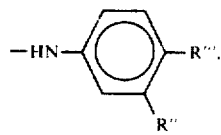

wherein R" is selected from the group consisting of hydrogen, halogen and lower fluorinated alkyl; R''' is selected from the group consisting of hydrogen, a halogen and a lower alkyl; with the proviso that when R is dl-α-methyl-β-phenylethyl and R' is H, and R" is Cl, then R''' can only be Cl; and when X is

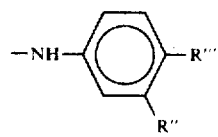

and R', R" and R''' are each hydrogen, then R can only be l-α-methyl-β-phenylethyl.

2. N-para-chlorophenylcarbamoyl-3-(β-phenylethyl)sydnonimine as claimed in claim 1 having the formula:

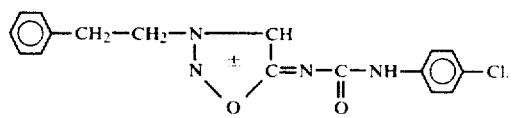

3. dl-N-para-chlorophenylcarbamoyl-3-(αmethyl-β-phenylethyl) sydnonimine as claimed in claim 1 having the formula:

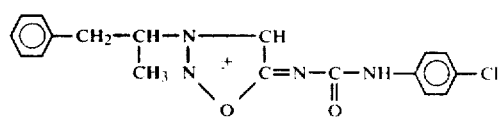

4. l-3(α-methyl-β-phenylethy)-N-phenylcarbamoyl-sydnonimine as claimed in claim 1 having the formula:

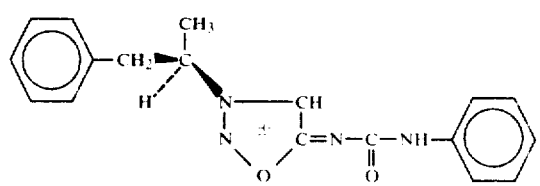

substantially free of its d-enantiomer.

5. l-N-para-chloro-phenylcarbamoyl-3-(α-methyl-β-phenylethyl) sydnonimine as claimed in claim 1 having the formula:

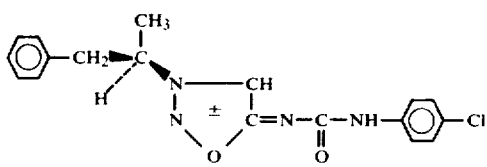

substantially free of its d-enantiomer.

6. A method for preparing N-acyl derivatives of sydnonimine of the formula:

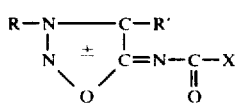

wherein R is selected from the group consisting of β-phenylethyl, dl-α-methyl-βphenylethyl and l-α-methyl-β-phenylethyl; R' is selected from the group consisting of hydrogen and phenyl; X is selected from the group consisting of lower alkyl, and

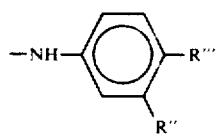

wherein R" is selected from the group consisting of hydrogen, halogen, and lower fluorinated alkyl; R''' is selected from the group consisting of hydrogen, halogen and lower alkyl; with the proviso that when R is dl-α-methyl-β-phenylethyl and R' is H, and R" is Cl, then R''' can only be Cl; and when X is

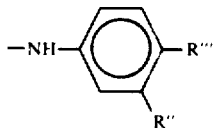

and R', R" and R''' are each hydrogen, then R can only be l-α-methyl-β-phenylethyl; comprising reacting N-nitroso derivatives of N-substituted nitriles of α-aminoacids of the formula:

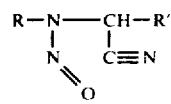

wherein R is selected from the group consisting of β-phenylethyl, dl-α-methyl-β-phenylethyl, and l-α-methyl-β-phenylethyl; R' is selected from the group consisting of H and phenyl; with an acylation agent selected from the group consisting of acyl halides of carboxylic acids, anhydrides of carboxylic acids, phenyl and substituted phenyl isocyanates, in a medium of a suitable organic solvent in the presence of a basic amine catalyst selected from the group consisting of tertiary amines, followed by isolation of the desired product.

7. A method as claimed in claim 6, wherein the process is conducted at a temperature of about 40° to 60° C.

8. The method of claim 16 wherein the solvent is selected from the group consisting of benzene, toluene, and dichloroethane.

9. The method of claim 16 wherein the basic amine catalyst is selected from the group consisting of triethylamine, dimethylbenzylamine, and N-methyl-morpholine.

10. The N-acyl sydnonimine of claim 10 wherein X is selected from the group consisting of methyl and

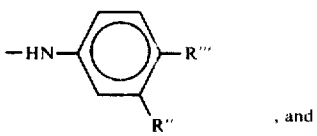
, and wherein R" is selected from the group consisting of hydrogen, halogen and fluorinated methyl; and R''' is selected from the group consisting of hydrogen, halogen and methyl.

11. The method of claim 6 wherein X is selected from the group consisting of methyl and

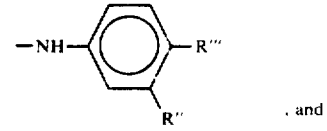
, and wherein R" is selected from the group consisting of hydrogen, halogen and fluorinated methyl; and R''' is selected from the group consisting of hydrogen, halogen and methyl.

* * * * *